(12) United States Patent
Yi et al.

(10) Patent No.: US 8,848,183 B2
(45) Date of Patent: Sep. 30, 2014

(54) APPARATUS HAVING NANO-FINGERS OF DIFFERENT PHYSICAL CHARACTERISTICS

(75) Inventors: Wei Yi, Mountain View, CA (US); Fung Suong Ou, Palo Alto, CA (US); Min Hu, Sunnyvale, CA (US); Wei Wu, Palo Alto, CA (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 134 days.

(21) Appl. No.: 13/188,941

(22) Filed: Jul. 22, 2011

(65) Prior Publication Data
US 2013/0021605 A1 Jan. 24, 2013

(51) Int. Cl.
*G01N 21/65* (2006.01)
*B82Y 20/00* (2011.01)
*B82Y 40/00* (2011.01)
*B82Y 15/00* (2011.01)

(52) U.S. Cl.
CPC ......... *G01N 21/658* (2013.01); *B82Y 40/00* (2013.01); *B82Y 20/00* (2013.01); *B82Y 15/00* (2013.01)
USPC .......................................................... 356/301

(58) Field of Classification Search
CPC .................................................. G01N 21/658
USPC .......................................................... 356/301
See application file for complete search history.

(56) References Cited

U.S. PATENT DOCUMENTS

| | | | |
|---|---|---|---|
| 6,286,226 B1 * | 9/2001 | Jin | 33/706 |
| 6,667,572 B2 * | 12/2003 | Lewis | 313/524 |
| 7,158,219 B2 * | 1/2007 | Li et al. | 356/36 |
| 7,189,430 B2 | 3/2007 | Ajayan et al. | |
| 7,256,435 B1 | 8/2007 | Kornilovich et al. | |
| 7,342,656 B2 * | 3/2008 | Islam et al. | 356/301 |
| 7,402,531 B1 | 7/2008 | Kuekes et al. | |
| 7,528,948 B2 * | 5/2009 | Bratkovski et al. | 356/301 |
| 7,650,052 B2 * | 1/2010 | Krishnamoorthy et al. | 385/14 |
| 2006/0231381 A1 | 10/2006 | Jensen et al. | |
| 2007/0252136 A1 | 11/2007 | Lieber et al. | |
| 2008/0017845 A1 | 1/2008 | Drndic et al. | |
| 2008/0098805 A1 | 5/2008 | Jin et al. | |
| 2008/0187648 A1 | 8/2008 | Hart et al. | |
| 2009/0261815 A1 | 10/2009 | Cairns et al. | |
| 2011/0116089 A1 * | 5/2011 | Schmidt et al. | 356/301 |

FOREIGN PATENT DOCUMENTS

| | | |
|---|---|---|
| CN | 101613076 | 12/2009 |
| CN | 101638228 | 2/2010 |
| EP | 2058908 | 5/2009 |

OTHER PUBLICATIONS

Wang et al. (Nano and microlens arrays grown using atomic-layer deposition); IEEE Photonics Technology Letters, vol. 18, No. 24; Dec. 15, 2006.*

Schreier et al. (Gaussian wave packets in resonant diffraction gratings); Optics in 1998/ Optics & Photonics News / Dec. 1998.*

(Continued)

*Primary Examiner* — Michael A Lyons
*Assistant Examiner* — Rufus Phillips (57) ABSTRACT

An apparatus includes a substrate and a plurality of nano-fingers attached at respective first ends to the substrate and freely movable along their lengths, in which a first set of the plurality of nano-fingers comprises a first physical characteristic, wherein a second set of the plurality of nano-fingers comprises a second physical characteristic, and wherein the first physical characteristic differs from the second physical characteristic.

12 Claims, 3 Drawing Sheets

(56) References Cited

OTHER PUBLICATIONS

Josef Giglmayr, Nano-Finger Electrodes for the Electro-Optical Generation and Tuning of Gratings at Several Wavelengths, <http://www.ipme.ru/ipme/conf/NN2003/NN2003_Abstract.pdf> Publication Date: August.

Kuo, Huei Pei et al., Vibrating Tip Surface Enhanced Raman Spectroscopy, U.S. Appl. No. 12/697,156, filed Jan. 29, 2010.

Stuke, Michael J. et al., Surface Enhanced Raman Spectroscopy Employing Vibrating Nanorods, U.S. Appl. No. 12/697,136, filed Jan. 29, 2010.

Wu, Wei et al., Apparatus for Performing SERS, U.S. Appl. No. 12/905,891, filed Oct. 15, 2010.

* cited by examiner

APPARATUS HAVING NANO-FINGERS OF DIFFERENT PHYSICAL CHARACTERISTICS

STATEMENT OF GOVERNMENT INTEREST

This invention was made with government support under Contract No. HR0011-09-3-0002, awarded by the Defense Advanced Research Projects Agency. The government has certain rights in the invention.

CROSS-REFERENCE TO RELATED APPLICATION

The present application contains some common subject matter with copending and commonly assigned U.S. patent application Ser. No. 12/905,891, titled "Apparatus for Performing SERS", filed on Oct. 15, 2010, the disclosure of which is hereby incorporated by reference in their entireties.

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman scattering.

Raman scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultraviolet portions of the electromagnetic spectrum.

Disclosed herein are an apparatus and a method for fabricating the apparatus. The apparatus includes a plurality of nano-fingers having different physical characteristics with respect to each other. The different physical characteristics include, for instance, different heights or lengths, different diameters, different compositions, etc. The differences in physical characteristics generally enable the apparatus to be implemented in various applications, including, fluid moving in microfluidic channels, molecule detection, etc.

Figure 1A:
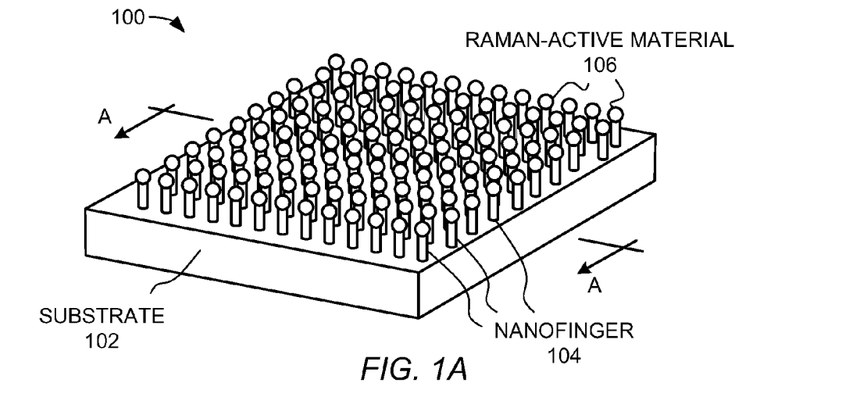
FIG. 1A shows an isometric view of an apparatus, according to an example of the present disclosure.

FIG. 1A shows an isometric view of an apparatus 100, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

According to an example, the apparatus 100 is to be used in sensing applications, for instance, to detect a molecule in an analyte sample with a relatively high level of sensitivity. For instance, the apparatus 100 may be employed in surface enhanced Raman spectroscopy (SERS), enhanced fluorescence, enhanced luminescence, etc., types of applications. In other examples, the apparatus 100 is to be used in various other types of applications, such as to move a relatively small amount of fluid.

The apparatus 100 is depicted as including a substrate 102 supporting a plurality of nano-fingers 104. The substrate 102 generally comprises any suitable material to support the nano-fingers 104, such as, glass, plastic, polymer, $SiO_2$, $Al_2O_3$, metal, etc. The nano-fingers 104 may be attached to the surface of the substrate 102 through any suitable attachment mechanism. For instance, the nano-fingers 104 may be grown directly on the substrate 102 surface through use of various suitable nano-structure growing techniques. As another example, the nano-fingers 104 may be integrally formed with the substrate 102. In this example, for instance, a portion of the material from which the substrate 102 is fabricated may be etched or otherwise processed to form the nano-fingers 104. In a further example, a separate layer of material may be adhered to the substrate 102 surface and the separate layer of material may be etched or otherwise processed to form the nano-fingers 104.

The nano-fingers 104 are formed of a relatively flexible material to enable the nano-fingers 104 to be laterally bendable, for instance, to enable free ends of the nano-fingers 104 to move toward each other, as discussed in greater detail herein below. Examples of suitable materials for the nano-fingers 104 include polymer materials, such as, polysiloxane, polyacrylate, polyimide, polyethylene, polypropelene, etc., or any combination thereof, metallic materials, such as, gold, silver, aluminum, etc., semiconductor materials, etc., and combinations thereof. In various examples, the nano-fingers 104 may be fabricated through a nanoimprinting or embossing process in which a template of relatively rigid pillars is employed in a multi-step imprinting process on a polymer matrix to form the nano-fingers 104. Various other processes, such as, etching, and various techniques used in the fabrication of micro-electromechanical systems (MEMS) and nano-electromechanical systems (NEMS) may also be used to fabricate the nano-fingers 104.

A nano-finger 104 may be defined as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 104 laterally onto one or more neighboring nano-fingers 104. In some examples, the length exceeds the cross sectional dimension (or width) by more than a factor of about 5 or 10. For example, the width may be about 100 nanometers (nm) and the height may be about 500 nm. In another example, the width at the base of the nano-finger 104 may range between about 10 nm and about 1 micron (μm) and the length may range between about 50 nm and 2 μm. In other examples, the nano-finger 104 is sized based upon the types of materials used to form the nano-finger 104. Thus, for instance, the more rigid the material(s) used to form the nano-finger 104, the less the width of the nano-finger 104 may be to enable the nano-finger 104 to be laterally collapsible. In further examples, the nano-finger 104 may form ridges in which two of three dimensions (for instance length and height) exceed by more than several times a nanoscale cross sectional dimension (for instance, width). According to particular examples, the nano-fingers 104 may equivalently be referenced as nanopoles or nanopillars without departing from a scope of the apparatus 100.

As shown in FIG. 1A, the nano-fingers 104 are arranged in an ordered array on the substrate 102. In this regard, the nano-fingers 104 may be distributed in a substantially uniform density on the substrate 102. Alternatively, however, at least some of the nano-fingers 104 may be randomly distributed on the substrate 102 to thereby vary the density of the nano-fingers 104 on the substrate 102. In any regard, and as discussed in greater detail herein below, the nano-fingers 104 are arranged with respect to each other such that the free ends of at least two neighboring nano-fingers 104 are able to touch each other when the nano-fingers 104 are in a collapsed state. By way of particular example, the neighboring nano-fingers 104 are positioned between about 10 to 500 nm apart from each other.

The nano-fingers 104 have been depicted as having substantially cylindrical cross-sections. It should, however, be understood that the nano-fingers 104 may have other shaped cross-sections, such as, for instance, oval, polygonal, rectangular, square, triangular, etc. In addition, or alternatively, the nano-fingers 104 may be formed with one or more features, such as, notches, bulges, etc., to substantially cause the nano-fingers 104 to be inclined to collapse in a particular direction. Thus, for instance, two or more adjacent nano-fingers 104 may include the one or more features to increase the likelihood that the nano-fingers 104 collapse toward each other. According to an example, the nano-fingers 104 are fabricated to be in the collapsed state under normal conditions and to be in an erect state when a stimuli is applied to the nano-fingers 104. According to another example, the nano-fingers 104 are fabricated to become collapsed when a stimuli is applied to the nano-fingers 104. Various manners in which the nano-fingers 104 may be moved between the collapsed and erect states are described in greater detail herein below.

According to an example, and as shown in FIG. 1A, the tips of the nano-fingers 104 each include Raman-active material 106. The Raman-active material 106 may be formed of a collection of atoms or atom clusters. In addition, the Raman-active material 106 may have a rough surface or a relatively smooth surface. Moreover, the Raman-active material 106 may have various other shapes than those depicted in FIG. 1A. For instance, the Raman-active material 106 may have relatively straight edges, remain within outer perimeters of the nano-fingers 104, etc.

It should also be noted that examples of the apparatus 100 are not limited to atoms or atom clusters disposed over just the tips of the nano-fingers 104. In other examples, the atoms or atom clusters of may be disposed over part of or nearly the entire surface of the nano-fingers 104. In any regard, the atoms or atom clusters may be deposited onto at least the free ends of the nano-fingers 104 through, for instance, physical vapor deposition (PVD), chemical vapor deposition (CVD), sputtering, etc., of metallic material, or self-assembly of pre-synthesized nano-particles. By way of example, the angle at which the atoms or atom clusters are deposited onto the free second ends of the nano-fingers 104 may be controlled to thereby substantially control the deposition of the atoms or atom clusters.

In some examples, a surface of the nano-fingers 104 and/or the Raman-active material 106 may be functionalized to facilitate adsorption of the analyte. For example, the tips or free ends of the nano-fingers 104 in a vicinity thereof (not illustrated) may be functionalized with a binding group to facilitate binding with a specific target analyte species. The functionalized surface (that is, either a surface of the nano-finger 104 itself and/or the Raman-active material 106 may provide a surface to which a particular class of analytes is attracted and may bond or be preferentially adsorbed. The functionalized surface may selectively bond with protein, DNA or RNA, biological or inorganic species, for example.

The Raman-active material 106 may comprise a metal, such as, gold, silver, copper, platinum, aluminum, etc., or a combination of these metals in the form of alloys, or other suitable material that is able to support surface plasmons for field enhancement for Raman scattering. In addition, the Raman-active material 106 may be multilayer structures, for example, 10 to 100 nm silver layer with 1 to 50 nm gold over-coating, or vice versa. In addition, or alternatively, the Raman-active material 106 may be further coated with a thin dielectric layer, or functional coating, such as ALD-grown silicon oxide or aluminum oxide, titanium oxide, etc. By definition herein, a Raman-active material is a material that supports surface plasmons and facilitates Raman scattering from an analyte adsorbed on or near a surface layer of the material during Raman spectroscopy.

Figure 1B:
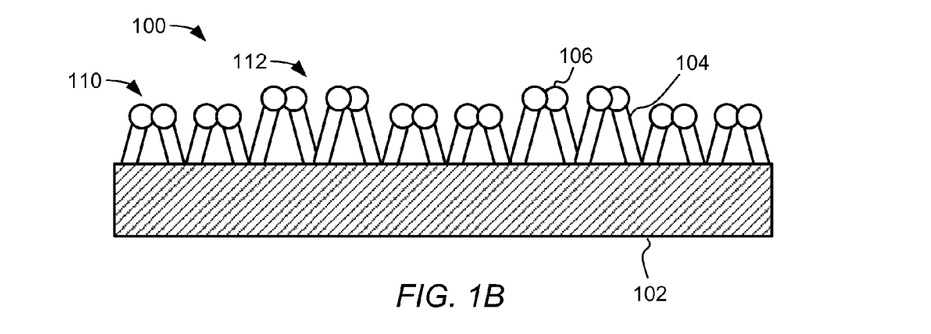
FIGS. 1B-1D, respectively, show cross-sectional views along a line A-A, shown in FIG. 1A of the apparatus, according to examples of the present disclosure.

Turning now to FIG. 1B, there is shown a cross-sectional view along a line A-A, shown in FIG. 1A, of the apparatus 100, in accordance with an example. As shown therein, adjacent pairs of the nano-fingers 104 are depicted as being collapsed toward each other, such that, the tips of some of the nano-fingers 104, and more particularly, some of the Raman-active material 106 are in contact with each other. In addition, a first set 110 of nano-fingers 104 is depicted as having a different physical characteristic than a second set 112 of nano-fingers 104. More particularly, the nano-fingers 104 in the first set 110 are depicted as having a relatively shorter length than the nano-fingers 104 in the second set 112. According to a particular example, the difference in length is greater than or equal to about 50 nm.

Figure 1C:
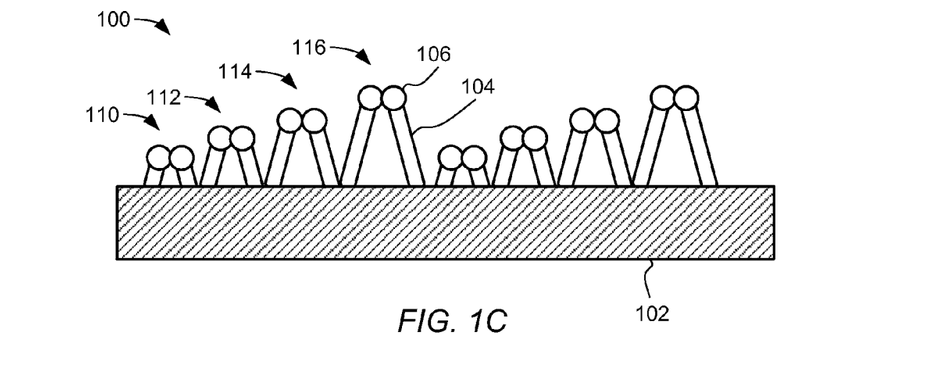

Turning now to FIG. 1C, there is shown a cross-sectional view along a line A-A, shown in FIG. 1A, of the apparatus 100, in accordance with another example. As shown in FIG. 1C, the apparatus 100 includes a third set 114 of nano-fingers 104 and a fourth set 116 of nano-fingers 104, in addition to the first and second sets 110 and 112. The nano-fingers 104 in the third set 114 are depicted as being relatively longer than the nano-fingers 104 in the first and second sets 110 and 112. In addition, the nano-fingers 104 in the fourth set 116 are depicted as being relatively longer than the nano-fingers 104 in the third set 114. According to a particular example, the differences in lengths between the nano-fingers 104 in each of the respective sets 110-116 are greater than or equal to about 50 nm.

As also shown in FIG. 1C, the nano-fingers 104 in each of the sets 110-116 are arranged in a predefined pattern. The predefined pattern is depicted as a repeating pattern composed of the nano-fingers 104 arranged in order of increasing height from left to right. Thus, for instance, the repeating pattern may be implemented to extend outward from a substantially central location of the substrate 102 to form concentric circles of the repeating pattern. According to other examples, the nano-fingers 104 may be arranged in different configurations on the substrate 102 according to their respective lengths. Examples of suitable configurations of the nano-fingers 104 having the 2 dimensional length modulation may include, for instance, holographic gratings, Fresnel lens, plasmonic nanostructures useful for laser light-beam conditioning, antenna, optical interconnects, etc.

Although FIGS. 1B and 1C depict the tips of two adjacent nano-fingers 104 having the same lengths being in contact with each other, it should be understood that the tips of a larger number of adjacent nano-fingers 104 may be in contact with each other, as may occur when a number of adjacent nano-fingers 104 collapse in multiple directions. In addition, it should be understood that the tips of adjacent nano-fingers 104 and/or the Raman-active material 106 included on the tips of the adjacent nano-fingers 104 having different lengths may be in contact with each other without departing from a scope of the apparatus 100.

Figure 1D:
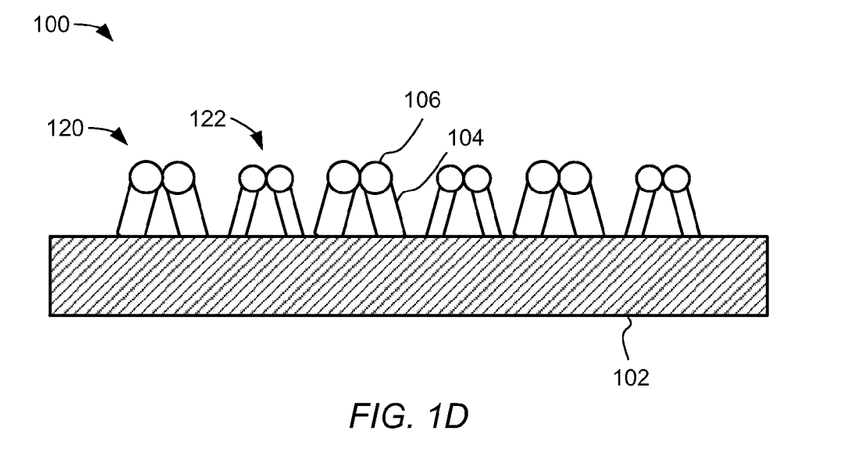

Turning now to FIG. 1D, there is shown a cross-sectional view along a line A-A, shown in FIG. 1A, of the apparatus 100, in accordance with a further example. As shown therein, adjacent pairs of the nano-fingers 104 are depicted as being collapsed toward each other, such that, the tips of some of the nano-fingers 104, and more particularly, some of the Raman-active material 106 are in contact with each other. In addition, a first set 120 of nano-fingers 104 is depicted as having a different physical characteristic than a second set 122 of nano-fingers 104. More particularly, the nano-fingers 104 in the first set 120 are depicted as having a relatively larger diameter than the nano-fingers 104 in the second set 120. According to a particular example, the difference in diameter is above about 50 nm. In addition, the nano-fingers 104 in the first and second sets may be arranged in any of a variety different configurations on the substrate 102.

Although not explicitly shown, the various sets of nano-fingers 104 depicted in FIGS. 1A-1D may include other types of physical characteristic differences. For instance, one set of the nano-fingers 104 may have a different cross-sectional shape than another set of the nano-fingers 104. As another example, one set of the nano-fingers 104 may have a different physical composition as compared with the physical composition of another set of the nano-fingers 104. As a further example, the sets of nano-fingers 104 may have multiple different physical characteristics with respect to each other.

The differences in physical characteristics between the nano-fingers 104 may also cause the various nano-fingers 104 to move from the collapsed state to the erect state or from the erect state to the collapsed state under application of different stimuli. For example, application of a first stimulus may cause the nano-fingers 104 in the first set 110, 120 to move from the collapsed state to the erect state, while the nano-fingers 104 in the second set 112, 122 remain in the collapsed state. In this example, a second stimulus may be applied to the apparatus 100 to cause the nano-fingers 104 in the second set 112, 122 to move from the collapsed state to the erect state. Examples of suitable stimuli include, for instance, various combinations or concentrations of chemicals designed to interact differently with the nano-fingers 104 in the different sets 110-122 of nano-fingers 104. Other examples of suitable stimuli include, for instance, fluids at different temperatures, in which the nano-fingers 104 in the different sets 110-122 are to move as their temperatures change. Further examples of suitable stimuli include, for instance, introduction of electric currents and/or electrostatic charges on the nano-fingers 104. Still further examples of suitable stimuli include, for instance, introduction of a fluid and evaporation of the fluid, which may cause the nano-fingers 104 in the different sets 110-122 to be drawn together at different rates due to differences in their flexibilities.

According to an example, at least one fluid supply source may be provided to apply the stimuli onto the nano-fingers 104. Thus, for instance, the fluid supply source may be positioned to deliver a predetermined fluid onto the nano-fingers 104, in which the predetermined fluid is known to interact with the nano-fingers 104 to cause the nano-fingers 104 to move from a collapsed state to an erect state and/or from an erect state to a collapsed state. In this example, the fluid supply source may supply different fluids or fluids having different compositions or characteristics onto the nano-fingers 104, in which the fluids interact with the nano-fingers 104 in the different sets 110-122 in different manners. Thus, for instance, a first fluid may cause the nano-fingers 104 in the first set 110, 120 to become erect, while being unable to cause the nano-fingers 104 in the other sets 112-116, 122 to become erect. In addition, a second fluid may separately be introduced that may cause the nano-fingers 104 in at least one of the other sets 112-116, 122 to become erect.

Figure 2:
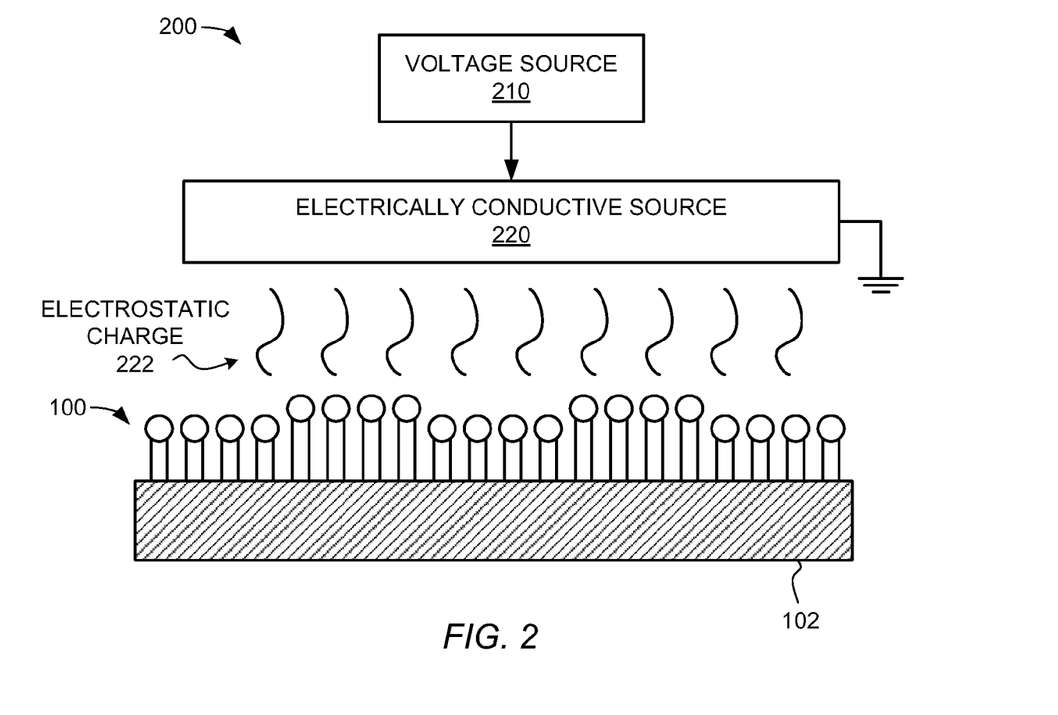
FIG. 2 shows a block diagram of a system for applying an electrostatic charge on the apparatus depicted in FIG. 1A, according to an example of the present disclosure.

With reference to FIG. 2, there is shown a system 200 for applying an electrostatic charge on the nano-fingers 104, according to an example. The system 200 is depicted as including a voltage source 210, an electrically conductive source 220, and the apparatus 100 of FIG. 1B. The system 200 may, however, include additional components or the components depicted therein may be modified or removed without departing from a scope of the system 200. Various manners in which the system 200, and variants thereof, may be implemented to apply electrostatic charges to move the nano-fingers 104 between collapsed and erect states are described in greater detail in U.S. patent application Ser. No. 12/905,891.

The voltage source 210 may comprise any suitable source from which alternating current (AC) or direct current (DC) voltage may be received. The electrically conductive source 220 may comprise any suitable component through the AC or DC voltage may be applied in relatively close proximity to the nano-fingers 104. Thus, for instance, the electrically conductive source 220 may comprise an electrode or wire positioned in relatively close proximity, without contacting, the nano-fingers 104. According to another example, the substrate 102 comprises the electrically conducive source 220.

The voltage source 210 is depicted in FIG. 2 as being activated or in an on state and is thus depicted as applying a voltage through the electrically conductive source 220 or the substrate 102. The application of the voltage through the electrically conductive source 220 is depicted as generating an electrostatic charge 222 onto the Raman-active material 106, thereby causing the Raman-active material 106 to become electrostatically charged with the same polarity. The Raman-active material 106 disposed on the ends of adjacent nano-fingers 104 thus repel each other, causing the nano-fingers 104 to be substantially erect.

According a particular example, the voltage source 210 may apply different levels of voltage across the electrically conductive source 220 to thereby vary the level of the electrostatic charge 222. In one regard, the different electrostatic charge 222 levels may affect the nano-fingers 104 in the different sets 110-122 differently. For instance, a lower electrostatic charge 222 level may cause the nano-fingers 104 in the first set 110, 120 to become erect, while being unable to cause the nano-fingers 104 in the other sets 112-116, 122 to become erect, so they remain in the collapsed state. In addition, a higher electrostatic charge 222 level may be applied to cause the remaining sets 112-116, 122 of nano-fingers 104 to also become erect. In one regard, therefore, the nano-fingers 104 in the different sets 110-122 may be controllably and sequentially manipulated. In the event that the nano-fingers 104 are arranged, for instance, as depicted in FIG. 1C, the sequential manipulation of the nano-fingers 104 in the different sets 110-116 may cause a fluid surrounding the nano-fingers 104 to be moved in a desired direction. In this regard, the apparatus 100 may be employed to move fluid, for instance, in a microfluidic channel.

According to an example, when the nano-fingers 104 are in substantially erect states, the free ends of the nano-fingers 104, and thus, the Raman-active material 106, are in a substantially spaced arrangement with respect to each other. The gaps between the free ends (Raman-active material 106) may be of sufficiently large size to enable a liquid to be supplied in the gaps. In addition, the gaps may be of sufficiently small size to enable the free ends (Raman-active material 106) of the nano-fingers 104 in each of the clusters 106 to move toward each other as the liquid evaporates, through, for instance, capillary forces applied on the free ends as the liquid dries. The free ends of adjacent ones of the nano-fingers 104 may also move toward each other, for instance, when application of the electrostatic charge 222 is ceased.

An analyte to be tested using the apparatus 100 may be included in the liquid to thus enable molecules from the analyte to be trapped between the tips (and/or the Raman-active material 106). Other non-limiting examples, such as e-beam, ion-beam, magnetic, mechanical force, thermal effect, or electric charge effect, may also be utilized to cause the ends of the nano-fingers 104 to move toward each other. In addition, the tips of the nano-fingers 104, and/or the Raman-active material 106 of respectively adjacent nano-fingers 104 may contact each other and remain in contact with each other through van der Waals interactions between those elements.

Figure 3:
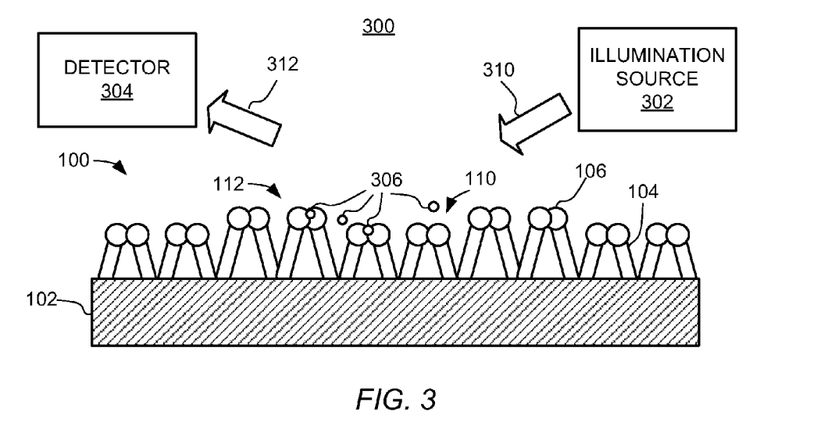
FIG. 3 shows a block diagram of a surface enhanced Raman spectroscopy (SERS) system, according to an example of the present disclosure.

With reference now to FIG. 3, there is shown a block diagram of a surface enhanced Raman spectroscopy (SERS) system 300, according to an example. It should be understood that the system 300 depicted in FIG. 3 may include additional components and that some of the components described herein may be removed and/or modified without departing from a scope of the system 300. It should also be understood that the components depicted in FIG. 3 are not drawn to scale and thus, the components may have different relative sizes with respect to each other than as shown therein.

As shown in FIG. 3, the SERS system 300 includes the apparatus 100 depicted in FIG. 1B, an illumination source 302, and a detector 304. The SERS system 300 may, however, include any of the other apparatuses 100 depicted in FIGS. 1C and 1D or an apparatus having a different configuration. In any regard, the apparatus 100 is depicted as including a first set 110 of nano-fingers 104 and a second set 112 of nano-fingers 104, in which the nano-fingers 104 in the second set 112 are longer than the nano-fingers 104 in the first set 110.

As also shown in FIG. 3, the nano-fingers 104 are depicted as being in the collapsed state. As discussed above, as the ends of the nano-fingers 104 move toward each other, analyte molecules 306 may become trapped between two or more of the contacting nano-fingers 104. In addition, the analyte molecules 306 may become trapped between nano-fingers 104 in respective sets 110 and 112 as depicted in FIG. 3.

The illumination source 302 is to emit an electromagnetic radiation, such as, visible light, onto the free ends of the nano-fingers 104, as represented by the arrow 310. By way of example, the illumination source 302 may comprise a laser that illuminates the free ends of the nano-fingers 104 with visible light. The electromagnetic radiation 310 is intended to cause the analyte molecules 306 to produce Raman scattered light as represented by the arrow 312. In addition, the detector 304 is positioned to detect the Raman scattered light 312 emitting from the analyte molecule(s) 306.

The Raman-active material 106 located near or adjacent to the analyte molecule(s) 306 may enhance the production of Raman scattered light from the analyte molecule(s) 306 by concentrating or otherwise enhancing an electromagnetic field in a vicinity of the analyte molecule(s) 306. The collapsing of two or more of the nano-fingers 104 upon each other to trap the analyte molecule(s) 306 may substantially increase the likelihood that the analyte molecule(s) 306 will be positioned near or in contact with some Raman-active material 106. In this regard, the likelihood that an analyte molecule(s) 306 will produce relatively strong Raman scattered light will thus also be increased. Thus, through implementation of the system 300, the detector 304 may receive a relatively stronger Raman scattered light signal 312 from the illuminated analyte molecule(s) 306 as compared with conventional SERS systems.

In addition, analyte molecules 306 trapped or positioned adjacent to Raman-active material 106 at different heights with respect to the substrate 102 may emit Raman scattered light at different intensities. As such, for instance, by illuminating analyte molecules 306 at different heights simultaneously, a substantially optimal illumination intensity may be obtained to thereby increase the likelihood that an analyte molecule(s) 306 will produce a relatively strong Raman scattered light 312. In one regard, the system 300 enables the simultaneous testing of nano-fingers 104 having different heights instead of having to perform multiple different tests using apparatuses having different nano-finger 104 heights. In another regard, the nano-fingers 104 may be arranged according to their varying heights, for instance, as shown in FIG. 1D, to cause the Raman scattered light 312 to be directed toward a particular direction and/or to be focused.

The detector 304 is to convert the Raman scattered light 312 emitted from the analyte molecule(s) 306 into electrical signals that may be processed to identify, for instance, the analyte. In some examples, the detector 304 is to output the electrical signals to other components (not shown) configured to process the electrical signals. In other examples, the detector 304 is equipped with processing capabilities to identify the analyte.

According to an example, the apparatus 100 includes the illumination source 302 and the detector 304, for instance, integrated onto a single chip. In this example, the apparatus 100 provides a relatively compact solution that may be implemented efficiently for a relatively large sensing area.

Figure 4:
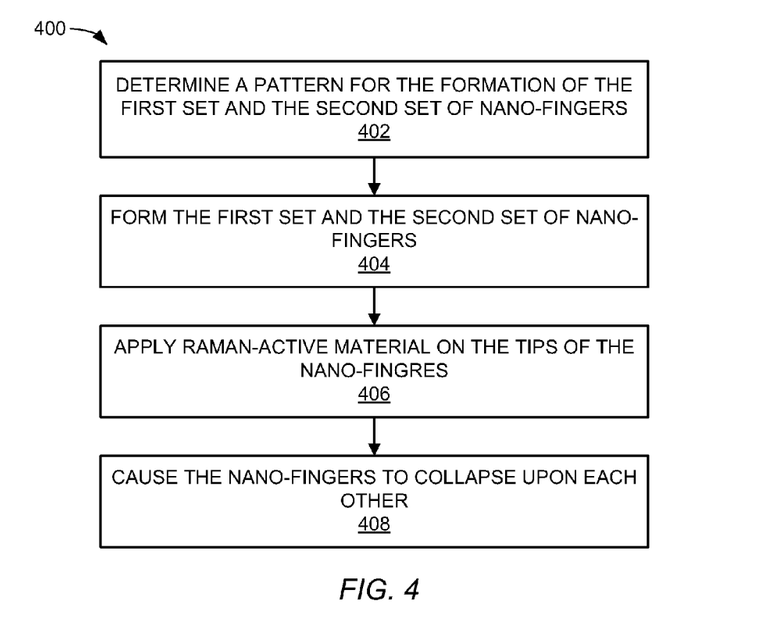
FIG. 4 shows a flow diagram of a method for fabricating an apparatus, for instance, the apparatus depicted in FIG. 1A, according to examples of the present disclosure.

Turning now to FIG. 4, there is shown a flow diagram of a method 400 for fabricating an apparatus, for instance, the apparatus 100 of FIGS. 1A-3, according to an example. It should be understood that the method 400 may include additional processes and that some of the processes described herein may be removed and/or modified without departing from a scope of the method 400. In addition, although particular reference is made herein to the apparatus 100 in implementing the method 400, it should be understood that the method 400 may be implemented through use of a differently configured apparatus without departing from a scope of the method 400.

At block 402, a pattern of the first set 110 of the plurality of nano-fingers 104 and of the second set 112 of the plurality of nano-fingers 104 is generated. The generation of the pattern may also include generation of placement for the nano-fingers 104 in additional sets 114, 116, 120, 122. In any regard, the pattern may be generated so that the nano-fingers 104 in the first set 110 are to be particularly positioned on the substrate 102 with respect to the nano-fingers 104 in the second set 112. The pattern may form, for instance, holographic gratings, Fresnel lens, plasmonic nanostructures useful for laser light-beam conditioning, antenna, optical interconnects, etc., on the substrate 102.

At block 404, the first set 110 of nano-fingers 104 and the second set 112 of nano-fingers 104 are formed on the substrate 102 according to the pattern determined at block 402. According to an example, a template or mold defining the determined pattern and the different physical characteristics of the different sets 110-122 of the nano-fingers 104 may be formed and transferred to the substrate 102. As another example, the nano-fingers 104 may be formed with the same physical characteristics and a masking and etching operation may be implemented on the respective nano-fingers 104 to vary the physical characteristics of the nano-fingers 104 to have the desired physical characteristics and arrangement on the substrate 102. In this regard, nano-fingers 104 having different physical characteristics with respect to each other may be fabricated on the substrate 102.

Alternatively, however, the first set 110 of nano-fingers 104 and the second set 112 of nano-fingers 104 may be formed on the substrate 102 in a substantially random manner. In this example, the determination of the pattern at block 402 may be omitted and the nano-fingers 104 having the first physical characteristic and the nano-fingers 104 having the second physical characteristic may be formed to be interspersed with each other on the substrate 102.

In any regard, and according to an example, a nanoimprinting technique or a roll-to-roll process may be implemented to form the nano-fingers 104 having the different physical characteristics with respect to each other on the substrate 102. In this example, a template may be formed through photolithography or other advanced lithography with a desired patterning and physical characteristic modulations of the first and second sets 110, 112 of nano-fingers 104. More particularly, for instance, the desired patterns may be designed on a mold, by E-beam lithography, photolithography, laser interference lithography, FIB (Focused Ion Beam), self-assembly of spheres, etc. In addition, the pattern may be transferred onto silicon, glass, or polymer substrate (PDMS, Polyethylene terephthalate, polyimide, polycarbonate, etc.). In other examples, the nano-fingers 104 may be formed in the predetermined arrangement through implementation of any suitable fabrication process.

At block 406, Raman-active material 106 is applied on the tips of the nano-fingers 104, for instance, by depositing atoms or atom clusters of the Raman-active material. The Raman-active material atoms or atom clusters may be deposited onto the tips of the nano-fingers 104 through, for instance, physical vapor deposition (PVD), chemical vapor deposition (CVD), sputtering, etc., of the Raman-active material, or self-assembly of pre-synthesized nano-particles. In certain examples in which the apparatus 100 is to be implemented as a fluid moving device and not an apparatus for certain sensing applications as discussed in greater detail herein above, block 406 may be omitted.

At block 408, the nano-fingers 104 are caused to collapse upon each other in any of the manners discussed above. According to an example, prior to collapsing of the nano-fingers 104, an analyte 306 (FIG. 3) is introduced onto the apparatus 100. In this example, the nano-fingers 104 may be caused to collapse upon each other to thereby trap molecules of the analyte 306 between respective ones of the Raman-active material 106. Alternatively, the nano-fingers 104 may be caused to collapse upon each other prior to introduction of the analyte 306. In any regard, a detection operation may be performed on the analyte 306 using the apparatus 100 as discussed above with respect to FIG. 3.

As also discussed in greater detail herein above, at block 408, the nano-fingers 104 in the first set 110 may be caused to collapse independently of the nano-fingers 104 in the second set 112. More particularly, for instance, the nano-fingers 104 in the first set 110 may collapse under application of different stimuli as compared with the nano-fingers 104 in the second set 112. In this regard, the apparatus 100 may be implemented as a fluid moving device in a microfluidic channel.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus comprising:
a substrate; and
a plurality of nano-fingers attached at respective first ends to the substrate, wherein a first set of the plurality of nano-fingers comprises a first physical characteristic, wherein a second set of the plurality of nano-fingers comprises a second physical characteristic that differs from the first physical characteristic, wherein the first physical characteristic comprises at least one of a length and a width and the second physical characteristic comprises at least one of a length and a width, wherein the first physical characteristic differs from the second physical characteristic, wherein the plurality of nano-fingers are composed of a flexible material, and wherein the first set of the plurality of nano-fingers and the second set of the plurality of nano-fingers are arranged on the substrate in a predetermined configuration that causes the plurality of nano-fingers to operate as at least one of a holographic grating, a Fresnel lens, and an optical interconnect lens, and thereby causes light that is at least one of emitted through and reflected from the plurality of nano-fingers to be modulated in a predetermined manner,
wherein the first set of the plurality of nano-fingers are to collapse independently of the second set of the plurality of nano-fingers.

2. The apparatus according to claim 1, wherein the first physical characteristic and the second physical characteristic comprise length, and wherein the first set of the plurality of nano-fingers comprises a length that differs by greater than or equal to about 50 nm from the length of the second set of the plurality of nano-fingers.

3. The apparatus according to claim 1, further comprising:
a plurality of first sets of the plurality of nano-fingers; and
a plurality of second sets of the plurality of nano-fingers.

4. The apparatus according to claim 3, wherein the plurality of first sets and the plurality of second sets are arranged in a repeating pattern.

5. The apparatus according to claim 1, wherein the plurality of nano-fingers have a length of in the range of about 50 nm to 2 μm, a diameter in the range of about 10 nm to 1 μm, and a spacing of about 10 to 500 nm at the base of the plurality of nano-fingers.

6. The apparatus according to claim 1, wherein Raman-active material is positioned on respective tips of the plurality of nano-fingers and wherein the plurality of nano-fingers are composed of flexible material and are able to be collapsed toward other ones of the plurality of nano-fingers, such that, gaps between the Raman-active material on the tips of at least two adjacent nano-fingers are reduced.

7. The apparatus according to claim 1, further comprising:
an illumination source to illuminate the plurality of nano-fingers; and
a detector positioned to detect Raman scattered light emitted from an analyte molecule positioned near the respective tips of the plurality of nano-fingers.

8. A method for fabricating an apparatus having a plurality of nano-fingers, said method comprising:
forming, on a substrate, a first set of the plurality of nano-fingers to comprise a first physical characteristic;
forming, on the substrate, a second set of the plurality of nano-fingers to comprise a second physical characteristic, wherein the first physical characteristic differs from the second physical characteristic, wherein the first physical characteristic comprises at least one of a length and a width and the second physical characteristic comprises at least one of a length and a width;
wherein forming the first set and the second set of the plurality of nano-fingers further comprises forming the first set and the second set of the plurality of nano-fingers in a predetermined configuration that causes the plurality of nano-fingers to operate as at least one of a holographic grating, a Fresnel lens, and an optical interconnect lens, and thereby causes light that is at least one of emitted through and reflected from the plurality of nano-fingers to be modulated in a predetermined manner; and
wherein the first set of the plurality of nano-fingers are to collapse independently of the second set of the plurality of nano-fingers.

9. The method according to claim 8, said method further comprising:
generating a pattern for formation of the first set of the plurality of nano-fingers and the second set of the plurality of nano-fingers on the substrate prior to forming the first set and the second set of the plurality of nano-fingers.

10. The method according to claim 9, further comprising:
forming a template defining the determined pattern;
transferring the template to the substrate; and
implementing a fabrication process to form the plurality of nano-fingers at the defined locations on the substrate and for the first set of the plurality of nano-fingers to have the first physical characteristic and the second set of the plurality of nano-fingers to have the second physical characteristic.

11. The method according to claim 8, further comprising:
applying Raman-active material on the tips of the plurality of nano-fingers; and
causing the plurality of nano-fingers to collapse toward other ones of the plurality of nano-fingers to cause the Raman-active material on the tips of at least two of the plurality of nano-fingers to contact each other.

12. A method for implementing an apparatus comprising a substrate and a plurality of nano-fingers attached at respective first ends to the substrate and freely movable along their lengths, wherein a first set of the plurality of nano-fingers comprises a first physical characteristic, wherein a second set of the plurality of nano-fingers comprises a second physical characteristic that differs from the first physical characteristic, wherein the first physical characteristic comprises at least one of a length and a width and the second physical characteristic comprises at least one of a length and a width, wherein the first physical characteristic differs from the second physical characteristic, wherein the plurality of nano-fingers are composed of a flexible material, and wherein the first set of the plurality of nano-fingers and the second set of the plurality of nano-fingers are arranged on the substrate in a predetermined configuration that causes the plurality of nano-fingers to operate as at least one of a holographic grating, a Fresnel lens, and an optical interconnect lens, and thereby causes light that is at least one of emitted through and reflected from the plurality of nano-fingers to be modulated in a predetermined manner said method comprising:
causing the first set of the plurality of nano-fingers to collapse independently of the second set of the plurality of nano-fingers; and
causing the second set of the plurality of nano-fingers to collapse.

* * * * *